United States Patent
Castelijns et al.

[11] Patent Number: 5,663,433
[45] Date of Patent: Sep. 2, 1997

[54] PROCESS FOR THE PREPARATION N-ALKYL-N,O-DIACETYL HYDROXYLAMINE

[75] Inventors: Anna M. C. F. Castelijns, Beek; Joannes M. C. A. Mulders, Geleen, both of Netherlands

[73] Assignee: DSM N.V., Heerleen, Netherlands

[21] Appl. No.: 668,074

[22] Filed: Jun. 17, 1996

Related U.S. Application Data

[63] Continuation of PCT/NL94/00318, Dec. 14, 1994.

[30] Foreign Application Priority Data

Dec. 16, 1993 [BE] Belgium ................................. 9301399

[51] Int. Cl.$^6$ .................................................. C07C 231/00
[52] U.S. Cl. ........................................................ 562/874
[58] Field of Search ............................................. 562/874

[56] References Cited

U.S. PATENT DOCUMENTS 5,371,264  12/1994  Manner et al. ........................ 562/874

OTHER PUBLICATIONS

Christensen et al., "Electrolytically Generated Nucleophiles," *Acta Chemica Scandinavica* B 33(1979) 352–358.

*Primary Examiner*—Peter O'Sullivan
*Attorney, Agent, or Firm*—Cushman Darby & Cushman IP Group of Pillsbury Madison & Sutro, LLP

[57] ABSTRACT

Process for the preparation of N-alkyl-N,O-diacetyl hydroxylamine, for instance N-methyl-N,O-diacetyl hydroxylamine, by catalytic reduction of a nitroalkane, for instance nitromethane, in the presence of acetic anhydride. As catalyst preferably a platinum on alumina catalyst is used. The invention provides a simple one-step process for the preparation of N-alkyl-N,O-diacetyl hydroxylamine in a relatively concentrated reaction medium.

9 Claims, No Drawings

PROCESS FOR THE PREPARATION N-ALKYL-N,O-DIACETYL HYDROXYLAMINE

This is a continuation of: International Appln. No. PCT/NL9400318 filed Dec. 14,1994 which designated the U.S.

The invention relates to a process for the preparation of an N-alkyl-N,O-diacetyl hydroxylamine from the corresponding nitroalkane.

Such a process is known from Klemm, L. H.; Acta Chem. Scand. Ser. B., 28 (1974) 593 and also from Christensen, L.; Acta Chem. Scand. Ser. B., 33 (1979) 352.

The known process involves the electrochemical reduction of a nitroalkane in acetic anhydride, which has as disadvantages that specific equipment is to be used. In addition, the reaction is carried out in strongly diluted reaction mixtures.

The invention now provides a process for obtaining N-alkyl-N,O-diacetyl hydroxylamine which does not have the above-mentioned disadvantages.

According to the invention this is achieved by subjecting the corresponding nitroalkane to a catalytic reduction in the presence of acetic anhydride.

While the above-mentioned articles also refer to a catalytic reduction of nitroarenes, not of nitroalkanes, in acetic anhydrides, it is stated, however, that this catalytic reduction is possible only with very limited success.

Nitroalkanes that are suitable for use are aliphatic compounds of the formula R—$NO_2$, where R represents an alkyl group, in particular an alkyl group with 1–5 carbon atoms, such as e.g. nitromethane.

In the catalytic reduction according to the invention use is made of a suitable hydrogenation catalyst, for instance a noble metal catalyst. Good results were obtained with a platinum catalyst. In practice such a catalyst is usually applied on a support, for instance a carbon, graphite or $Al_2O_3$ support. Preferably, platinum on $Al_2O_3$ is used as catalyst. The amount of catalyst that is used is not critical; the optimum amount can readily be determined. Thus, for instance, starting from a 5 wt.% Pt/$Al_2O_3$ catalyst use is preferably made of 0.2–1wt.% of catalyst, calculated relative to the amount of nitroalkane. In principle the catalyst can be recycled.

The temperature and the pressure at which the reduction is carried out are not critical. Mostly, a temperature between 20° and 100° C., preferably 70°–80° C., and a (hydrogen) pressure of 1–9 MPa, preferably 5–8 MPa, will be used. Higher pressures often lead to faster reactions, but sometimes also to a lower selectivity.

Theoretically, 3 moles of acetic anhydride per mole of nitroalkane are needed for the reaction. For a satisfactory reaction usually a molar ratio of acetic anhydride to nitroalkane in excess of 3 is used; the molar ratio of acetic anhydride to nitroalkane preferably lies between 3.5 and 5.

Instead of a nitroalkane, in the reaction according to the invention the starting material used may also be the aldoxime formed as an intermediate product in this reaction. Thus, formaldoxime can be used instead of nitromethane.

The reaction mixture obtained after reduction can be processed in a known manner. Besides N-methyl-N,O-diacetyl hydroxylamine the mixture usually contains N-methylacetamide, which is difficult to separate by distillation, and therefore the reaction mixture is preferably contacted with a suitable acylating agent. This results in acylation of the N-methylacetamide, so that it is easier to separate it from N-methyl-N,O-diacetyl hydroxylamine. The acylation usually takes place at a temperature between 100° and 180° C., in particular between 150° and 160° C. Examples of suitable acylating agents are anhydrides and carboxylic acid chlorides. The preferred acylating agent is acetic anhydride.

EXAMPLE I

A high-pressure reactor (V=200 ml) equipped with a mechanical stirrer was successively fed with 0.36 g 3% Pt/$Al_2O_3$ (Johnson Matthey, type 94), 86.7 g acetic anhydride (0.85 mol) and 12.8 g nitromethane (0.21 mol). The autoclave was then purged with $N_2$ and hydrogen was used to raise its pressure to 4 MPa. The reaction mixture was subsequently heated slowly until the hydrogenation started (t=about 65° C.). The temperature was then raised to 69° C. and the pressure was set at 5 MPa using $H_2$. Under these conditions hydrogenation took place for six hours. After this, the reaction mixture was cooled to room temperature and its pressure relieved. After the catalyst had been filtered off the reaction mixture was analyzed gas chromatographically. It was found that 95% of the nitromethane had been converted, the selectivity to N-methyl-N, O-diacetylhyam and N-methylacetamide being 53% and 43%, respectively.

The crude reaction mixture was refluxed with acetic anhydride. This resulted in the N-methylacetamide being converted quantitatively to N-methyl-N-acetylacetamide, while the N-methyl-N,O-diacetylhyam remained unchanged in the reaction mixture. Distillation of the mixture thus obtained (sieve tray column with 20 plates, Rv=10) yielded a main fraction (bpt. 93°–95° C.; 18.7×$10_3$ Pa), which consisted to more than 99% of N-methyl-N,O-diacetylhyam.

EXAMPLE II–VIII

Using a procedure analogous to that described for Example I, the following experiments were conducted. The results are presented in Table 1.

TABLE 1

| Ex. | cat. type | cat (g) | $CH_3NO_2$ (mol) | $Ac_2O$ (mol) | t (°C.) | p (MPa) | t (hrs) | conv. $CH_3NO_2$ (%) | sel. hyam[1] | sel. amide[2] |
|---|---|---|---|---|---|---|---|---|---|---|
| II | a | 0.36 | 0.21 | 0.85 | 90 | 5 | 2.25 | 100 | 50 | 46 |
| III | a | 0.36 | 0.21 | 0.85 | 71–78 | 8 | 2.5 | 90 | 45 | 52 |
| IV | a | 0.36[3] | 0.21 | 0.87 | 68 | 5 | 7.5 | 71 | 60 | 37 |
| V | a | 0.12 | 0.21 | 0.85 | 67 | 5 | 7.3 | 94 | 51 | 40 |
| VI | a | 0.18 | 0.11 | 0.85 | 68 | 5 | 5 | 26 | 50 | 28 |
| VII | a | 0.44 | 0.21 | 0.85 | 69 | 5 | 5 | 100 | 44 | 49 |
| VIII | a | 0.12 | 0.21 | 0.85 | 66 | 5 | 2.2 | 82 | 39 | 52 | a: 5% Pt/$Al_2O_3$; Johnson Matthey type 94
b: 5% Pt/C; Engelhard code 99805

TABLE 1-continued

| Ex. | cat. type | cat (g) | CH$_3$NO$_2$ (mol) | Ac$_2$O (mol) | t (°C.) | p (MPa) | t (hrs) | conv. CH$_3$NO$_2$ (%) | sel. hyam[1] | sel. amide[2] |
|---|---|---|---|---|---|---|---|---|---|---| c: 5% Pt/graphite; Johnson Matthey type 287
[1]: hyam = N-methyl-N,O-diacetylhyam
[2]: amide = N-methylacetamide
[3]: catalyst used a 2nd time

We claim:

1. Process for the preparation of an N-alkyl-N,O-diacetyl hydroxylamine from the corresponding nitroalkane, characterized in that the nitroalkane is subjected to a catalytic reduction in the presence of acetic anhydride.

2. Process according to claim 1, characterized in that nitromethane is used as nitroalkane.

3. Process according to either of claims 1–2, characterized in that a noble metal catalyst is used as catalyst.

4. Process according to claim 3, characterized in that a supported platinum catalyst is used as catalyst.

5. Process according to claim 4, characterized in that Al$_2$O$_3$ is used as support.

6. Process according to any one of claims 1–5, characterized in that the reduction is carried out at a temperature between 20° and 100° C.

7. Process according to any one of claims 1–6, characterized in that the reduction is carried out at a pressure between 1 and 9 MPa.

8. Process according to any one of claims 1–7, characterized in that the reaction mixture obtained after reduction is subjected to a treatment with an acylating agent.

9. Process according to claim 8, characterized in that acetic anhydride is used as acylating agent.

* * * * *